US012699081B2

(12) United States Patent
Onuma et al.

(10) Patent No.: US 12,699,081 B2
(45) Date of Patent: Aug. 4, 2026

(54) METHOD OF MEASURING STABLE HEMOGLOBIN A1c AND MEASUREMENT DEVICE THEREFOR

(71) Applicant: ARKRAY, Inc., Kyoto (JP)

(72) Inventors: Naotsugu Onuma, Kyoto (JP); Tomoyuki Matsuda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 400 days.

(21) Appl. No.: 18/224,927

(22) Filed: Jul. 21, 2023

(65) Prior Publication Data

US 2024/0036028 A1 Feb. 1, 2024

(30) Foreign Application Priority Data

Jul. 26, 2022 (JP) ................................. 2022-118897

(51) Int. Cl.
*G01N 33/49* (2006.01)

(52) U.S. Cl.
CPC .................................... *G01N 33/49* (2013.01)

(58) Field of Classification Search
CPC ...................................................... G01N 33/49
See application file for complete search history.

(56) References Cited

U.S. PATENT DOCUMENTS

| | | | |
|---|---|---|---|
| 2019/0120790 A1 | 4/2019 | Kawano et al. | |
| 2019/0120803 A1 | 4/2019 | Hasegawa | |
| 2020/0400690 A1 | 12/2020 | Shigemitsu et al. | |

FOREIGN PATENT DOCUMENTS

| | | |
|---|---|---|
| JP | H09-264889 A | 10/1997 |
| JP | 2012-215470 A | 11/2012 |
| JP | 2016-183871 A | 10/2016 |
| JP | 2017-203677 A | 11/2017 |

(Continued)

OTHER PUBLICATIONS

Little, Randie R et al., "Effects of Hemoglobin (Hb) E and HbD Traits on Measurements of Glycated Hb (HbA1c) by 23 Methods," Clinical Chemistry, vol. 54, Issue 8, Aug. 1, 2008, pp. 1277â1282, https://doi.org/10.1373/clinchem.2008.103580 (Year: 2008).*

(Continued)

*Primary Examiner* — Andrew Schechter
*Assistant Examiner* — Ethan Wesley Edwards
(74) *Attorney, Agent, or Firm* — Morgan, Lewis & Bockius LLP

(57) ABSTRACT

A method of measuring stable hemoglobin A1c by a hemoglobin separation analysis method based on cation exchange, the method comprising: obtaining an analysis signal from a blood specimen to be measured by the separation analysis method; determining a C value, which is a peak value of a stable hemoglobin A1c peak, and an X value, which is a peak value of a specific peak appearing between the stable hemoglobin A1c peak and a hemoglobin A0 peak, from the analysis signal; and correcting the C value by applying the C value and the X value to a predetermined arithmetic expression to obtain a C' value that is a reduced value from the C value, wherein the arithmetic expression is determined based on a correlation between a C value and an X value obtained from a blood specimen in which a stable hemoglobin A1c value is known by the separation analysis method.

18 Claims, 12 Drawing Sheets

(56)     References Cited

FOREIGN PATENT DOCUMENTS

JP      2019-078599  A     5/2019
JP      2021-001804  A     1/2021

OTHER PUBLICATIONS

Mosca, Andrea et al., "Feasibility of an EQAS for HbA1c in Italy using fresh blood samples" Clinical Chemistry and Laboratory Medicine (CCLM), vol. 52, No. 7, 2014, pp. e151-e153. https://doi.org/10.1515/cclm-2014-0084 (Year: 2014).*

Radin MS. "Pitfalls in hemoglobin A1c measurement: when results may be misleading." J Gen Intern Med. Feb. 2014;29(2):388-94. doi: 10.1007/s11606-013-2595-x. Epub Sep. 4, 2013. PMID: 24002631; PMCID: PMC3912281. (Year: 2013).*

Extended European Search Report issued in the corresponding Application No. 23187002.3, dated Jan. 3, 2024.

Office Action issued in the corresponding European Application No. 23187002.3, dated Jul. 15, 2025.

Office Action issued in the corresponding Japanese Application No. 2022-118897, dated Mar. 24, 2026.

Office Action issued in the corresponding European Patent Application No. 23187002.3, dated Apr. 22, 2026.

* cited by examiner

START $R_1 = a \times X + b$    S20

$C' = C - C \times R_1$    S25

END

FIG.10

METHOD OF MEASURING STABLE HEMOGLOBIN A1c AND MEASUREMENT DEVICE THEREFOR

CROSS-REFERENCE TO RELATED APPLICATION

This application claims priority under 35 USC 119 from Japanese Patent Application No. 2022-118897, filed on Jul. 26, 2022, the disclosure of which is incorporated by reference herein.

BACKGROUND

Technical Field

The present disclosure relates to a method of measuring stable hemoglobin A1c in a blood specimen, and a measurement device therefor.

Related Art

There are plural types of hemoglobin in a blood sample, and in addition to normal hemoglobin (hemoglobin A), there are plural types of hemoglobin variants (hemoglobin C, hemoglobin D, hemoglobin E, hemoglobin S, etc.) also referred to as abnormal hemoglobin. For the measurement of hemoglobin, electrophoresis (Japanese Patent Application Laid-Open (JP-A) No. 2019-078599) and liquid chromatography (Japanese Patent Application Laid-Open (JP-A) No. H09-264889) are used.

In a case in which a blood sample containing hemoglobin E as abnormal hemoglobin is measured by cation exchange chromatography, a hemoglobin E peak is detected between a stable hemoglobin A1c peak and a hemoglobin A0 peak. In a case in which the blood sample contains hemoglobin E, the stable hemoglobin A1c peak (peak area) decreases. As a result, it has been reported that a stable hemoglobin A1c value shows a value lower than an accurate stable hemoglobin A1c value. Therefore, in order to obtain the accurate stable hemoglobin A1c value, correction to increase the hemoglobin A1c value is performed (Japanese Patent Application Laid-Open (JP-A) No. 2012-215470 and Japanese Patent Application Laid-Open (JP-A) No. 2016-183871).

Furthermore, in a case in which a blood sample containing hemoglobin C, hemoglobin D, or hemoglobin S as abnormal hemoglobin is measured, correction is similarly performed in order to obtain an accurate stable hemoglobin A1c value (Japanese Patent Application Laid-Open (JP-A) No. 2017-203677). That is, when a hemoglobin A1c value of a specimen containing such abnormal hemoglobin is measured, a part of these abnormal hemoglobin components is eluted simultaneously with or after hemoglobin A0 which is a non-glycosylated component of hemoglobin A. Therefore, even if a significant peak corresponding to abnormal hemoglobin is excluded from the calculation of the stable hemoglobin A1c value, a phenomenon occurs in which the stable hemoglobin A1c value shows a low value. For such a phenomenon, in the technology described in JP-A No. 2017-203677, correction is performed so as to increase the hemoglobin A1c value on the basis of an area value of abnormal hemoglobin.

SUMMARY

In a case in which a sample having a known stable hemoglobin A1c value is measured using a conventional measurement device, a phenomenon in which a measured value becomes higher than a stable hemoglobin A1c value as a true value is often confirmed. As a result of verification by the present inventors, a phenomenon has been identified in which a measured value of stable hemoglobin A1c increases when a time-degraded specimen is used in a separation analysis method based on cation exchange as a principle.

An embodiment of the present disclosure provides a measurement method capable of measuring a stable hemoglobin A1c value that is closer to a true value by, for a specimen with an increase in a value of the stable hemoglobin A1c, removing as much as possible the influence of the increase by subtracting the influence of the increase from a measured value of the stable hemoglobin A1c, for example, in a case in which the specimen is subjected to alteration such as time degradation.

An embodiment of the present disclosure is a method of measuring stable hemoglobin A1c by a hemoglobin separation analysis method based on cation exchange as a principle, the method including: obtaining an analysis signal from a blood specimen to be measured by the separation analysis method; determining a C value, which is a peak value of a stable hemoglobin A1c peak, and an X value, which is a peak value of a specific peak appearing between the stable hemoglobin A1c peak and a hemoglobin A0 peak, from the analysis signal; and correcting the C value by applying the C value and the X value to a predetermined arithmetic expression to obtain a C' value that is a reduced value from the C value, wherein the arithmetic expression is determined based on a correlation between a C value and an X value obtained from a blood specimen in which a stable hemoglobin A1c value is known by the separation analysis method.

BRIEF DESCRIPTION OF THE DRAWINGS

Exemplary embodiments will be described in detail based on the following figures, wherein:

FIG. 10 is a graph illustrating a correlation between a temporal variation rate of the C value and the X value;

DETAILED DESCRIPTION

Figures 1A, 1B:
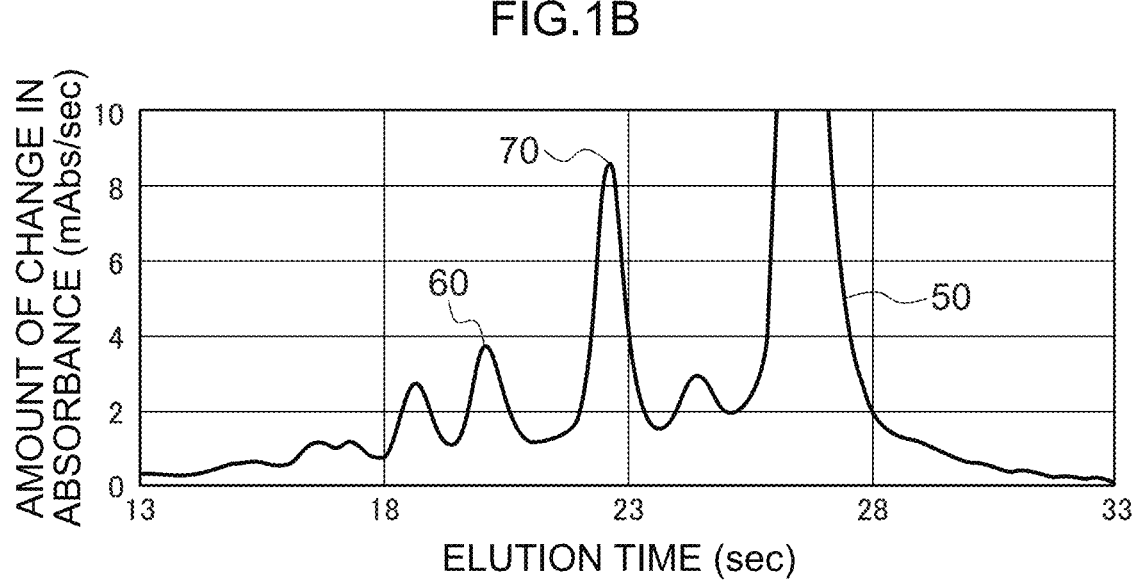
FIG. 1A is an electropherogram on the day of blood collection for Specimen 1.
FIG. 1B is an electropherogram 28 days after blood collection for Specimen 1.

Hereinafter, exemplary embodiments of the present disclosure will be described with reference to the drawings. The same reference signs in the drawings indicate the same portions even without any particular description. Note that a "peak value" in the present disclosure is a height or an area of each peak observed in an electropherogram as an analysis signal, and a relative value can be used therefor, and an absolute value can also be used therefor. This relative value may be a ratio to a whole area of the electropherogram, may be a ratio of a whole peak area related to hemoglobin in the electropherogram, or may be a ratio to an area of a specific peak (for example, hemoglobin A0 peak). Note that the analysis signal may be not only an electropherogram but also a chromatogram. The meaning of the "peak value" in that case is the same as described above.

Furthermore, in the following description, hemoglobin A0 is referred to as "HbA0", and stable hemoglobin A1c is referred to as "s-HbA1c". Moreover, in an electropherogram of hemoglobin observed by subjecting a human-derived blood specimen to capillary electrophoresis, peaks attributed to HbA0 and s-HbA1c are referred to as an "HbA0 peak" and an "s-HbA1c peak", respectively. Furthermore, peak values for the HbA0 peak and the s-HbA1c peak, and a "specific peak" to be described later are referred to as an "HbA0 peak value", an "s-HbA1c peak value", and a "specific peak value", respectively.

FIG. 1A and FIG. 1B are an electropherogram of hemoglobin measured by capillary electrophoresis based on cation exchange as a principle on the day of blood collection for Specimen 1 among blood specimens of Examples described later (FIG. 1A), and an electropherogram of hemoglobin measured in the same manner 28 days after blood collection (FIG. 1B). In FIG. 1A and FIG. 1B, an HbA0 peak 50 around an elution time of 27 seconds and an s-HbA1c peak 60 around an elution time of 20 seconds are observed.

Then, in FIG. 1B, a peak that is not observed in FIG. 1A appears around an elution time of 22.5 seconds between the s-HbA1c peak 60 and the HbA0 peak 50. This peak is referred to as a "specific peak 70". Although the reason why the specific peak 70 appears is unknown, the specific peak 70 may appear in a deteriorated blood specimen such as a blood specimen that has been subject to time degradation after a lapse of days from the day of blood collection. The specific peak 70 is a peak that appears at a detection time more than 0 and less than 1, preferably 0.01 or more and less than 0.8, more preferably 0.1 or more and less than 0.65, and still more preferably 0.2 or more and less than 0.5 (0.41 in FIG. 1B), providing that a peak top detection time of the s-HbA1c peak 60 is 0 and a peak top detection time of the HbA0 peak 50 is 1.

As shown in Examples described later, when hemoglobin of blood specimens stored for various days is measured by capillary electrophoresis based on cation exchange as a principle, a positive correlation is observed between the s-HbA1c peak value and the specific peak value.

As described above, a method of measuring s-HbA1c according to the present exemplary embodiment is based on a hemoglobin separation analysis method based on cation exchange as a principle, and includes a step of obtaining an analysis signal from a blood specimen to be measured by the separation analysis method, a step of determining a C value, which is a peak value of a stable hemoglobin A1c peak, and an X value, which is a peak value of a specific peak appearing between the stable hemoglobin A1c peak and a hemoglobin A0 peak, from the analysis signal, and a step of correcting the C value by applying the C value and the X value to a predetermined arithmetic expression to obtain a C' value obtained that is a reduced value from the C value. Then, the arithmetic expression is determined based on a correlation between the C value and the X value obtained from the blood specimen having a known stable hemoglobin A1c value by the separation analysis method.

The arithmetic expression may include, for example, an arithmetic step of obtaining a Y value, which is a value obtained by multiplying an X value obtained from a blood specimen to be measured by an A value that is a slope of a regression line between a C value and an X value obtained from plural the blood specimens having known s-HbA1c values, and an arithmetic step of obtaining a C' value by subtracting the Y value from the C value obtained from the blood specimen to be measured. Note that the regression lines between the C values and the X values may be obtained for each of the plural blood specimens, and an average value of the slopes may be set as the A value.

That is, the C value and the X value are measured for each of the plural blood specimens having a known s-HbA1c value, and the A value is obtained in advance as the slope of the regression line between the plural C values and the plural corresponding X values. Then, for the blood specimen to be measured, an analysis signal is obtained by the separation analysis method described above, and the C value and the X value are measured. The C value and the X value are applied to, for example, an arithmetic expression illustrated in the flowchart of FIG. 2.

Specifically, in the step shown in S10, as shown in the following Formula (1), a value obtained by multiplying the X value measured in the blood specimen to be measured by the A value is the Y value.

$$Y = A \times X \tag{1}$$

This Y value is considered to be a value corresponding to an amount by which the C value is raised from the true value according to the X value. Therefore, next, in the step shown in S15, as shown in the following Formula (2), the C' value, which is a value obtained by subtracting the Y value from the C value measured in the blood specimen to be measured, is obtained, so that the C value is reduced.

$$C'=C-Y \qquad (2)$$

Note that the Y value obtained by the above Formula (1) may overestimate the raised bottom of the C value with respect to the true value, or may underestimate the raised bottom of the C value. In such a case, the Y value may be corrected to an appropriate value by correcting the A value of the above Formula (1), correcting the X value, adding or subtracting an arbitrary value to or from the product of the A value and the X value, or using two or more of these in combination.

Apart from the above, the arithmetic expression may include, for example, an arithmetic step in which the X value obtained from the blood specimen to be measured is applied to a correlation between a temporal variation rate of the C value obtained from the blood specimen having the known s-HbA1c value and the X value to obtain an $R_1$ value that is a variation rate of the C value, and an arithmetic step in which a value obtained by multiplying the C value obtained from the blood specimen to be measured by the $R_1$ value is subtracted from the C value to obtain the C' value.

That is, the C value and the X value are measured in advance for each of the plural blood specimens having a known s-HbA1c value. At this time, the C value and the X value are measured for the same blood specimen from the day of blood collection to the day after storage for a predetermined number of days. Then, a correlation, for example, a regression line between a temporal variation rate, which is a rate at which the C value after storage for a predetermined number of days varies with respect to the C value on the day of blood collection, and the plural X values corresponding thereto is obtained in advance. Here, providing that the temporal variation rate is represented by y and the X value is represented by x, the regression line is represented by the following Formula (3).

$$y=ax+b \qquad (3)$$

Figure 3:
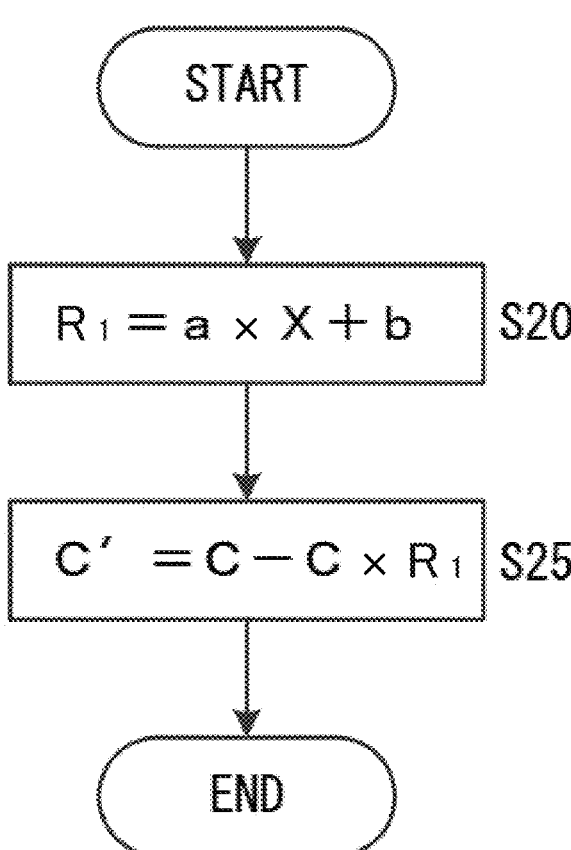
FIG. 3 is a flowchart illustrating a second example of the arithmetic expression.

Here, a in the above Formula (3) is a slope of the regression line, and b is an intercept of the regression line. Then, an analysis signal is obtained by the separation analysis method described above, and the C value and the X value of the blood specimen to be measured are measured. The C value and the X value are applied to the arithmetic expression illustrated in a flowchart of FIG. 3.

Specifically, in the step shown in S20, as shown in the following Formula (4), y obtained by substituting an X value for x in the above Formula (3) is an $R_1$ value.

$$R_1=a \times X+b \qquad (4)$$

The $R_1$ value is a temporal variation rate of the C value corresponding to the X value. Next, in the step shown in S25, as shown in the following Formula (5), a value obtained by multiplying the C value measured in the blood specimen to be measured by the $R_1$ value is subtracted from the C value, so that the C value is reduced.

$$C'=C-C \times R_1 \qquad (5)$$

Note that, in the $R_1$ value obtained by the above Formula (4), the C value may be excessively reduced in the correction performed by the above Formula (5), or conversely, the reduction may be too small. In such a case, the $R_1$ value may be corrected to an appropriate value by correcting the value of a in the above Formula (4), correcting the value of b, correcting the X value, or using two or more of these in combination.

The arithmetic expression may include a correlation table determined based on a correlation between the C value and the X value obtained from a blood specimen having a known s-HbA1c value by the separation analysis method. For example, from the X value and the C value measured in the blood specimen to be measured, a value or a ratio corresponding to the raised amount may be obtained using a correlation table, and the C' value may be obtained by subtracting the value from the C value. Alternatively, the Y value of the above Formula (1) may be obtained from the X value and the C value measured in the blood specimen to be measured using the correlation table, and the C' value may be obtained by subtracting the Y value from the C value. Alternatively, the $R_1$ value of the above Formula (4) may be obtained from the X value and the C value measured in the blood specimen to be measured based on the correlation table, and the C' value may be obtained by subtracting a value obtained by multiplying the C value by the $R_1$ value from the C value.

Here, providing that a peak top detection time of the s-HbA1c peak is 0 and a peak top detection time of the HbA0 peak is 1, the specific peak is preferably a peak appearing at the detection time more than 0 and less than 1, preferably 0.01 or more and less than 0.8, more preferably 0.1 or more and less than 0.65, and still more preferably 0.2 or more and less than 0.5.

For example, in FIG. 1(B), providing that the time point of the elution time of 20 seconds, which is the peak top detection time of the s-HbA1c peak 60, is 0, and the time point of the elution time of 26.6 seconds, which is the peak top detection time of the HbA0 peak 50, is 1, the time point of the elution time of 22.7 seconds, which is the peak top detection time of the specific peak 70, is 0.41.

The increase in the C value is a phenomenon observed when the specific peak appears. That is, as the X value, which is the peak value of the specific peak, increases, the C value rises and increases. Note that the reason why the specific peak appears is unknown, but the specific peak may appear in a deteriorated blood specimen such as a blood specimen that has been subject to time degradation after a lapse of days from the day of blood collection. Therefore, from the viewpoint of not unnecessarily correcting the C value for the blood specimen that is not deteriorated, a threshold value of the X value may be provided as to whether or not to perform correction. Then, in a case in which the X value exceeds a threshold value (for example, 5% for total hemoglobin), the C value may be corrected using the arithmetic expression described above.

Figure 4:
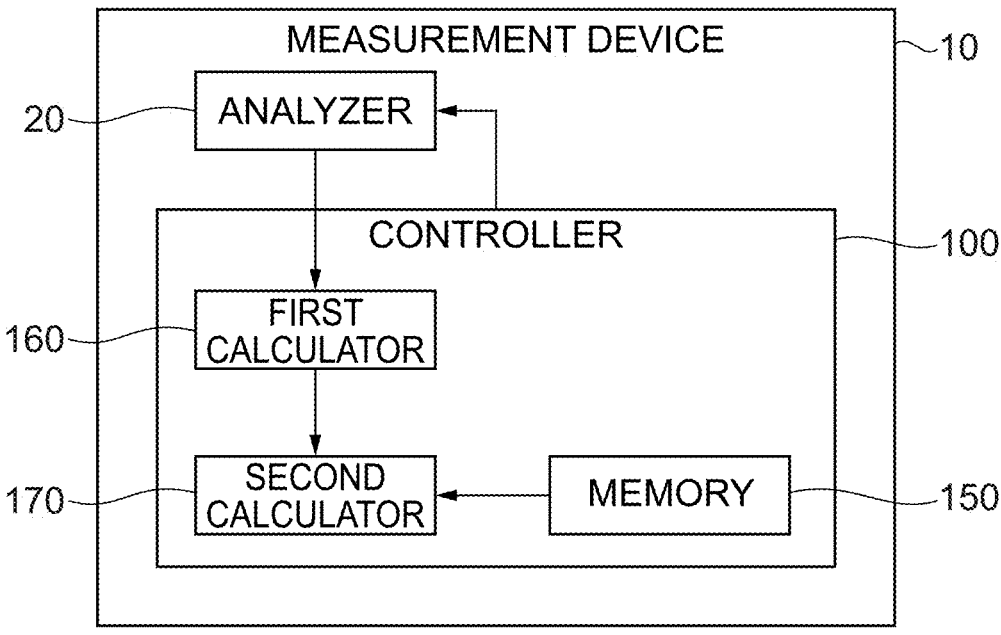
FIG. 4 is a block diagram of a measurement device according to the exemplary embodiment.

As illustrated in FIG. 4, a measurement device 10 for s-HbA1c of the present exemplary embodiment includes: a memory 150 that stores an arithmetic expression determined in advance based on a correlation between a C value, which is a peak value of an s-HbA1c peak, and an X value, which is a peak value of a specific peak appearing between the s-HbA1c peak and an HbA0 peak, by subjecting a blood specimen having a known s-HbA1c value to a hemoglobin separation analysis method based on cation exchange as a principle; an analyzer 20 that obtains an analysis signal by subjecting a blood specimen to be measured to the hemoglobin separation analysis method based on cation exchange as a principle; a first calculator 160 that obtains, from the analysis signal, a C value, which that is a peak value of the stable hemoglobin A1c peak, and an X value, which that is a peak value of a specific peak appearing between the stable hemoglobin A1c peak and the hemoglobin A0 peak, from the analysis signal; and, a second calculator 170 that calculates a C' value that is a reduced value from the C value, obtained by applying the C value and the X value to the arithmetic expression and reducing the C value.

The analyzer 20 is a device that performs separation analysis of hemoglobin based on cation exchange as a principle, and for example, a capillary electrophoresis device or a liquid chromatography device is used for the analyzer 20. The analyzer 20 separates hemoglobin into components by cation exchange, and outputs signal data corresponding to each of the components in the form of, for example, an electropherogram (in the case of a capillary electrophoresis device) or a chromatogram (in the case of a liquid chromatography device).

A controller 100 includes a memory 150, a first calculator 160, and a second calculator 170, controls the analyzer 20, and performs various calculations on the basis of the signal data output from the analyzer 20.

Figure 5:
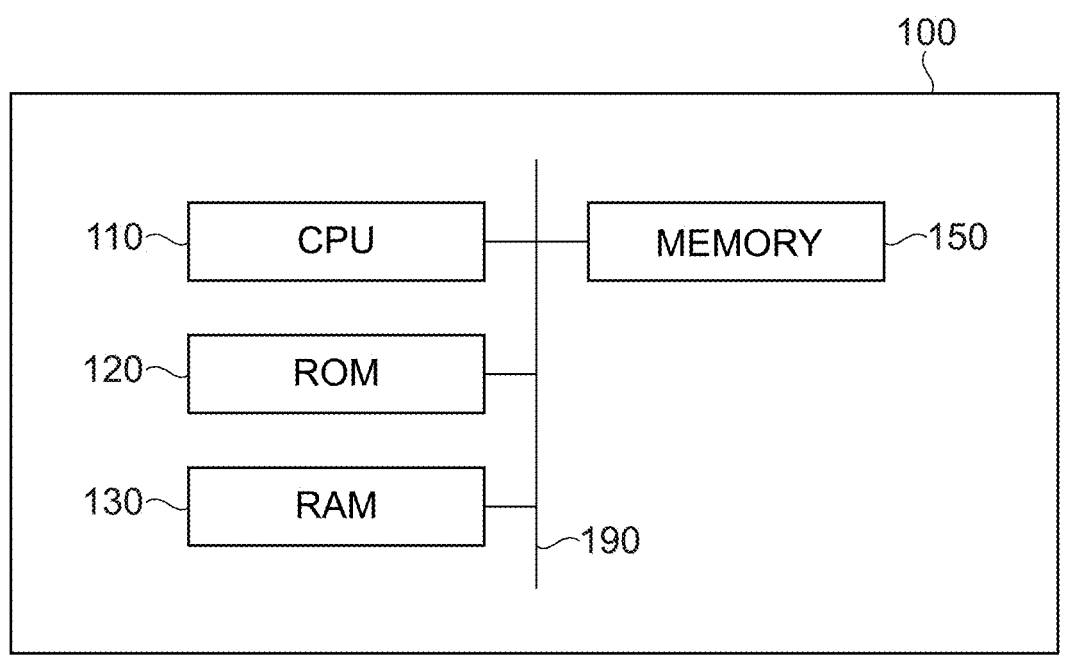
FIG. 5 is a block diagram of a controller.

As illustrated in the hardware configuration of FIG. 5, the controller 100 includes a central processing unit (CPU) 110, a read only memory (ROM) 120, a random access memory (RAM) 130, and the memory 150. The respective configurations are communicably connected to each other via a bus 190.

The CPU 110 is a central processing unit, and executes various programs and controls each unit. That is, the CPU 110 reads a program from the ROM 120 or the memory 150, and executes the program using the RAM 130 as a work area. The CPU 110 controls the analyzer 20 according to the program recorded in the ROM 120 or the memory 150.

The ROM 120 stores various programs and various data. The RAM 130 temporarily stores programs or data as a work area. The memory 150 is configured as a storage by a hard disk drive (HDD), a solid state drive (SSD), or a flash memory, and stores various programs including an operating system and various data. In the present exemplary embodiprogrammable logic device (PLD) and an application specific integrated circuit (ASIC) in which a circuit configuration can be changed after manufacturing a field-programmable gate array (FPGA) or the like. Furthermore, the processing of measuring s-HbA1c may be executed by one of these various processors, or may be executed by a combination of two or more processors of the same type or different types (for example, a combination of plural FPGAs or CPUs and FPGAs, or the like.). Furthermore, more specifically, the hardware structure of these various processors is an electric circuit in which circuit elements such as semiconductor elements are combined.

According to the embodiment of the present disclosure, there is provided a measurement method capable of measuring a stable hemoglobin A1c value closer to a true value by removing the influence of an increase in the value of the stable hemoglobin A1c as much as possible with respect to a specimen in which the value of the stable hemoglobin A1c has increased, for example, as in a case where the specimen is subjected to deterioration such as time degradation.

EXAMPLES (1) Measurement Data

For each of three subjects, venous blood was collected into nine blood collection tubes containing an anticoagulant (see Table 1 below) to obtain whole blood specimens (Specimen 1, Specimen 2, and Specimen 3). On the day of collection, the specimens were subjected twice to measurement of the C value and the X value on Day 0 using a capillary electrophoresis device (the Lab 001, Arkray). Thereafter, the specimens were stored under the condition of −20° C., and the C value and the X value were measured twice after 1 day, 3 days, 7 days, 14 days, and 28 days from the storage, respectively.

TABLE 1

| Product Name | Manufacturer | Anticoagulant/Glycolysis Inhibitor |
|---|---|---|
| VENOJECT II VP-H100K | Terumo | Heparin-Na |
| VENOJECT II VP-HL050K | Terumo | Heparin-Li |
| VENOJECT II VP-NA050K | Terumo | EDTA-2Na |
| VENOJECT II VP-DK052K | Terumo | EDTA-2K |
| VENOJECT II VP-TK052K | Terumo | EDTA-3K |
| Vacuum-sealed Blood Collection Tube NP-FN0205 | Nipro | NaF + EDTA-2Na |
| Vacuum-sealed Blood Collection Tube NP-FN0205 | Nipro | NaF + Heparin-Na |
| VENOJECT II VP-FH052K | Terumo | NaF + Heparin-Na + EDTA-2Na |
| VENOJECT II VP-CA050K70 | Terumo | 3.2% Sodium Citrate | ment, the ROM 120 or the memory 150 stores programs and various data related to control and calculation. The various data also include the arithmetic expression described above.

In the controller 100, the CPU 110 in the hardware configuration executes the program described above, and first, as the first calculator 160, obtains the C value and the X value from an analysis signal from the analyzer 20. Then, as the second calculator 170, applying the C value and the X value to the arithmetic expression stored in the memory 150, the CPU 110 calculates the C' value by reducing the C value.

Figure 6A:
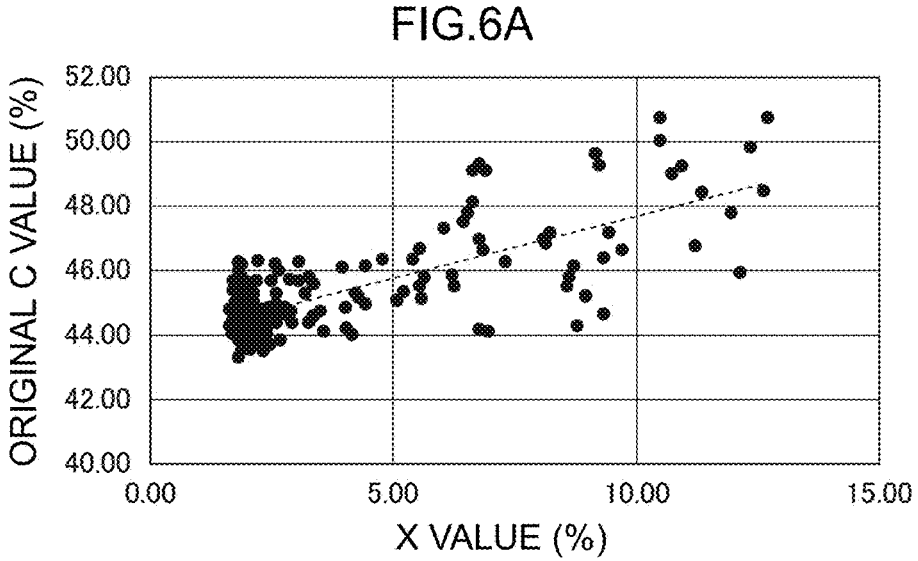
FIG. 6A is a graph illustrating a correlation between an X value and an original C value for Specimen 1.
Figure 6B:
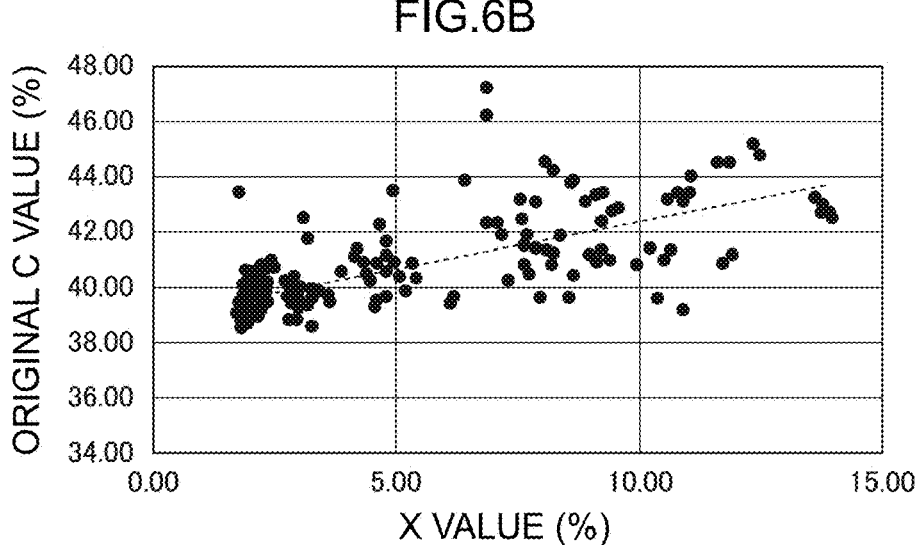
FIG. 6B is a graph illustrating a correlation between an X value and an original C value for Specimen 2.
Figure 6C:
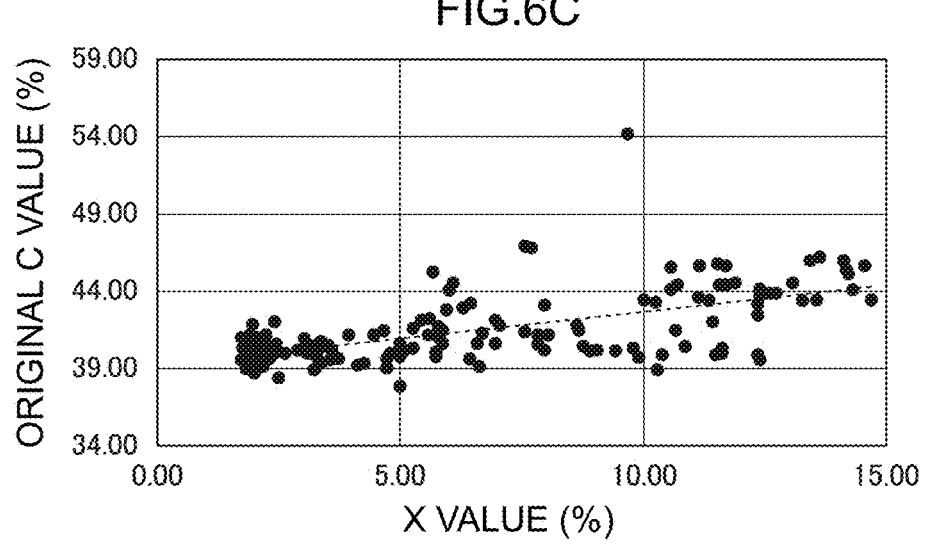
FIG. 6C is a graph illustrating a correlation between an X value and an original C value for Specimen 3.

Note that the processing of measuring s-HbA1c that the CPU 110 reads and executes the program may be executed by various processors other than the CPU 110. Examples of the processor in this case include a dedicated electric circuit which is a processor having a circuit configuration exclusively designed for executing specific processing such as a (2) First Correction Method FIG. 6A to FIG. 6C are graphs obtained by plotting a total of 108 sets of data obtained by performing measurement twice for each of 6 test points with the 9 types of blood collection tubes for each of Specimen 1 (FIG. 6A), Specimen 2 (FIG. 6B), and Specimen 3 (FIG. 6C), with the horizontal axis representing the X value and the vertical axis representing the measurement raw value (original C value, unit: %) of the C value. A broken line in each graph is a regression line between the X value and the original C value. The slopes of the regression line were 0.382 for Specimen 1, 0.348 for Specimen 2, and 0.339 for Specimen 3. Furthermore, positive correlation was found in all of the correlation coefficients of the regression lines of 0.744 for Specimen 1, 0.715 for Specimen 2, and 0.637 for Specimen 3.

Figure 2:
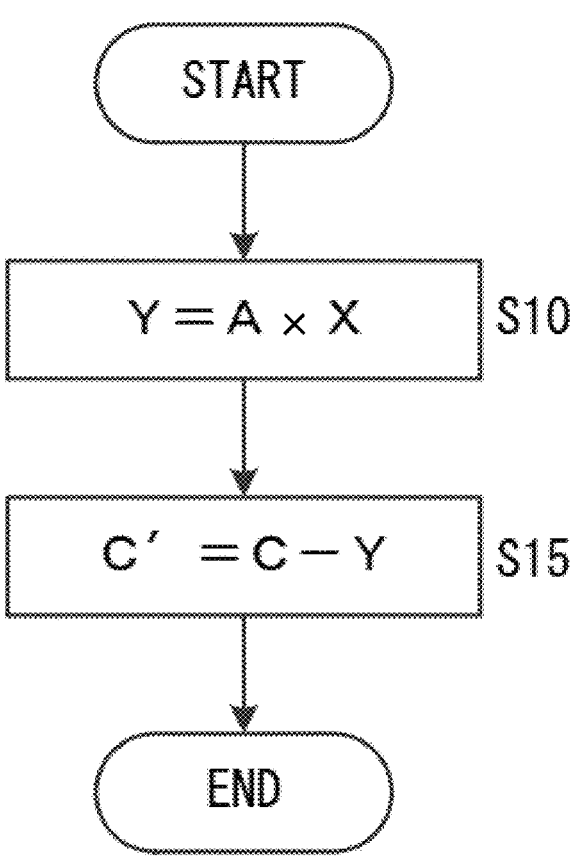
FIG. 2 is a flowchart illustrating a first example of an arithmetic expression.
Figure 7A:
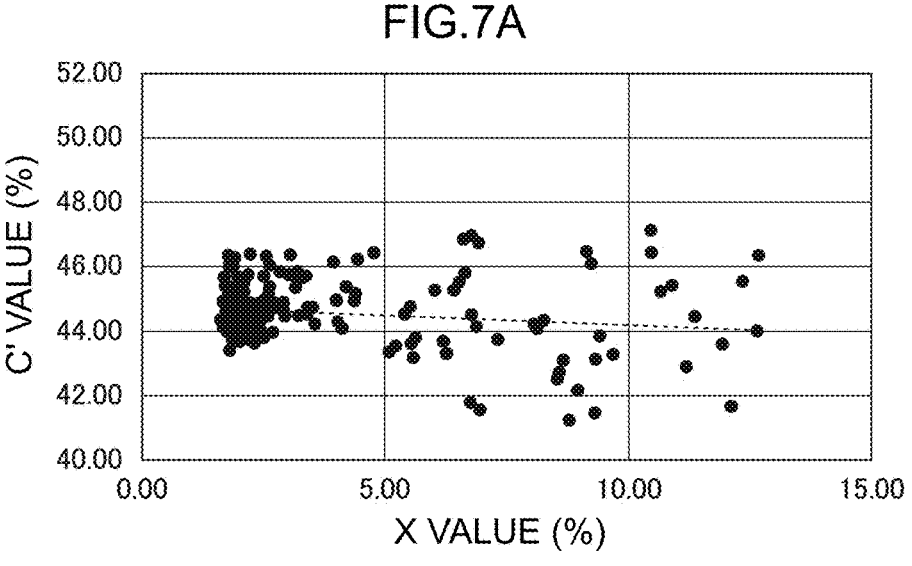
FIG. 7A is a graph illustrating a correlation between an X value and a C' value for Specimen 1.
Figure 7B:
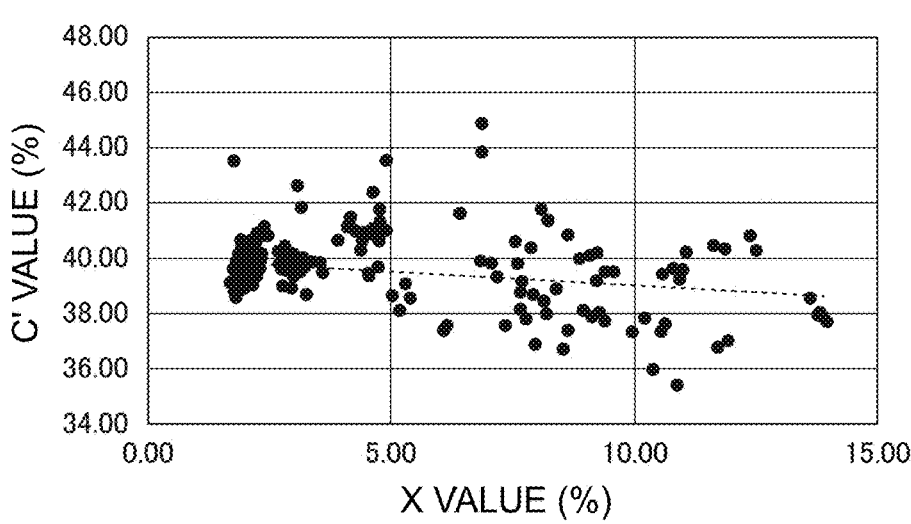
FIG. 7B is a graph illustrating a correlation between an X value and a C' value for Specimen 2.
Figure 7C:
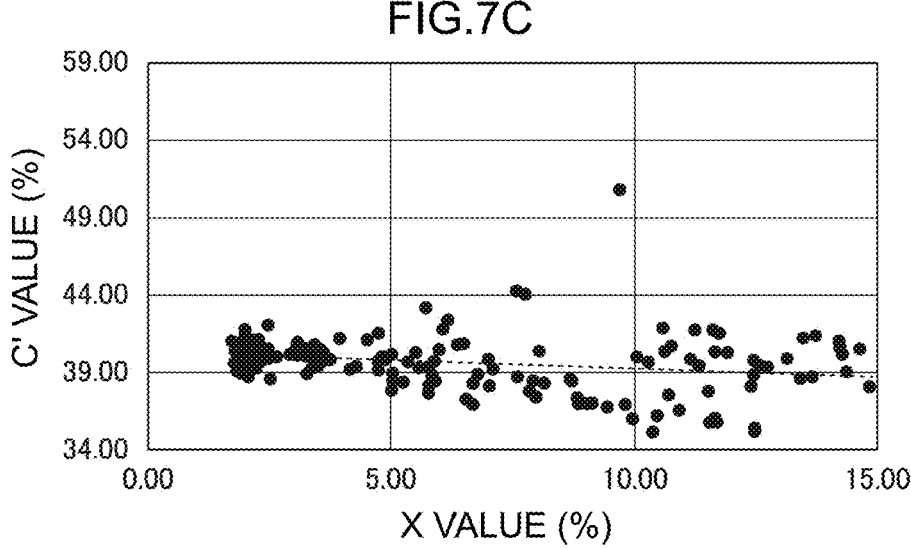
FIG. 7C is a graph illustrating a correlation between an X value and a C' value for Specimen 3.

Then, FIG. 7A to FIG. 7B are graphs in which a Y value is obtained by multiplying the X value obtained from the blood specimen to be measured in FIG. 6A to FIG. 6C by 0.356 as A in FIG. 2, which is an average value of the slopes, and a C' value corrected by subtracting the Y value from the C value obtained from the same blood specimen and reducing the C value is plotted in association with the X value in the same manner as in FIG. 6A to FIG. 6C. A broken line in each graph is a regression line between the X value and the C' value. The slopes of the regression line were –0.072 for Specimen 1, –0.103 for Specimen 2, and –0.106 for Specimen 3. Furthermore, the correlation coefficients of the regression lines were –0.200 for Specimen 1, –0.276 for Specimen 2, and –0.252 for Specimen 3.

The average value, the standard deviation, and the coefficient of variation are shown in Table 2 below after converting each data before correction and after correction of each of Specimen 1 to Specimen 3 from the measurement raw value to the international standardized value.

TABLE 2

| | Before Correction | | | After Correction | | |
| Specimen | Average | Standard Deviation | Coefficient of Variation | Average | Standard Deviation | Coefficient of Variation |
| --- | --- | --- | --- | --- | --- | --- |
| 1 | 5.79 | 0.14 | 2.36 | 5.72 | 0.10 | 1.67 |
| 2 | 5.36 | 0.15 | 2.85 | 5.26 | 0.12 | 2.24 |
| 3 | 5.40 | 0.19 | 3.49 | 5.27 | 0.15 | 2.83 |

From Table 2 above, it has been found that the data variation is leveled by the correction from the original C value to the C' value, and the increase in the C value accompanying the increase in the X value caused by the storage of the specimen is suppressed.

(3) Second Correction Method

Figure 8A:
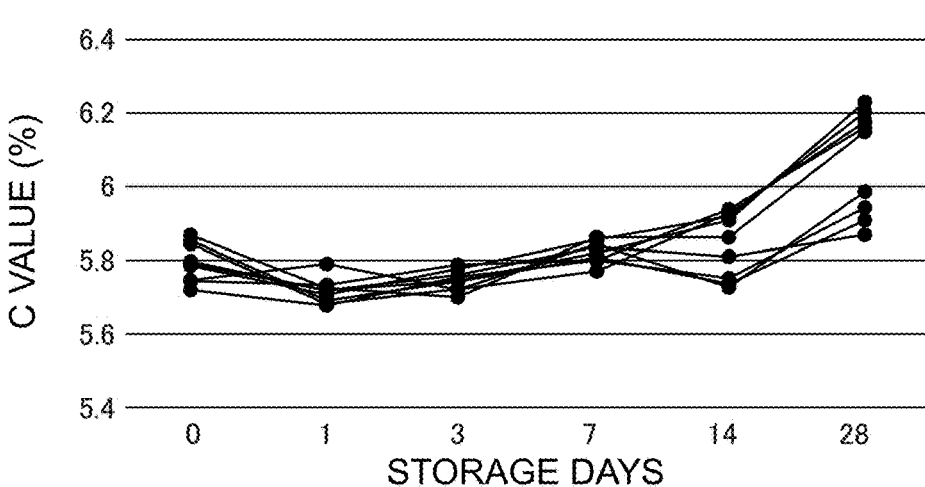
FIG. 8A is a graph illustrating a temporal change in the C value for Specimen 1.
Figure 8B:
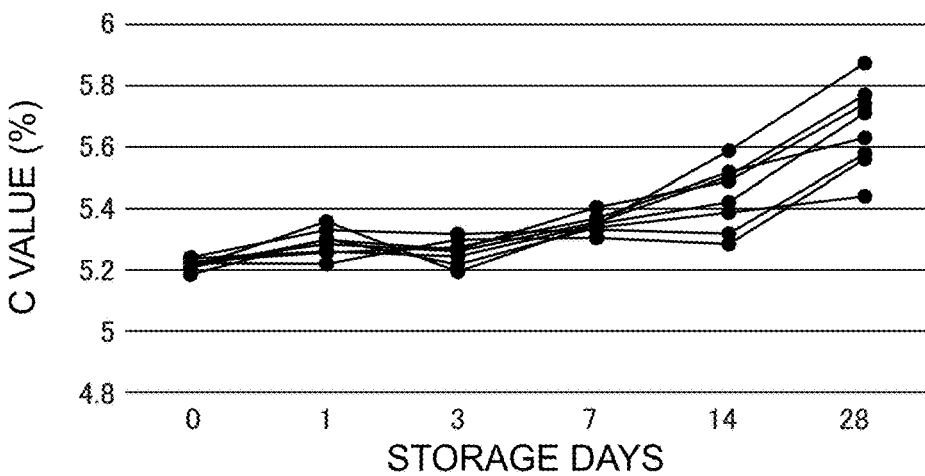
FIG. 8B is a graph illustrating a temporal change in the C value for Specimen 2.
Figure 8C:
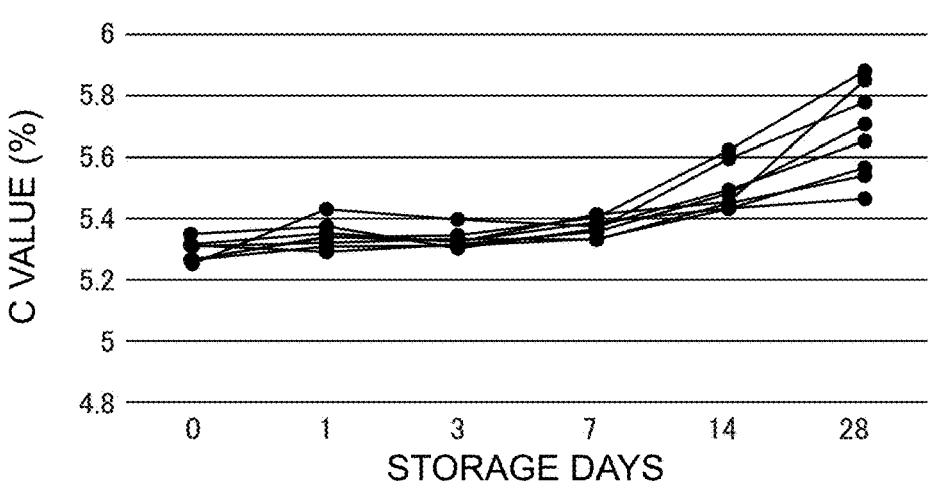
FIG. 8C is a graph illustrating a temporal change in the C value for Specimen 3.
Figure 9A:
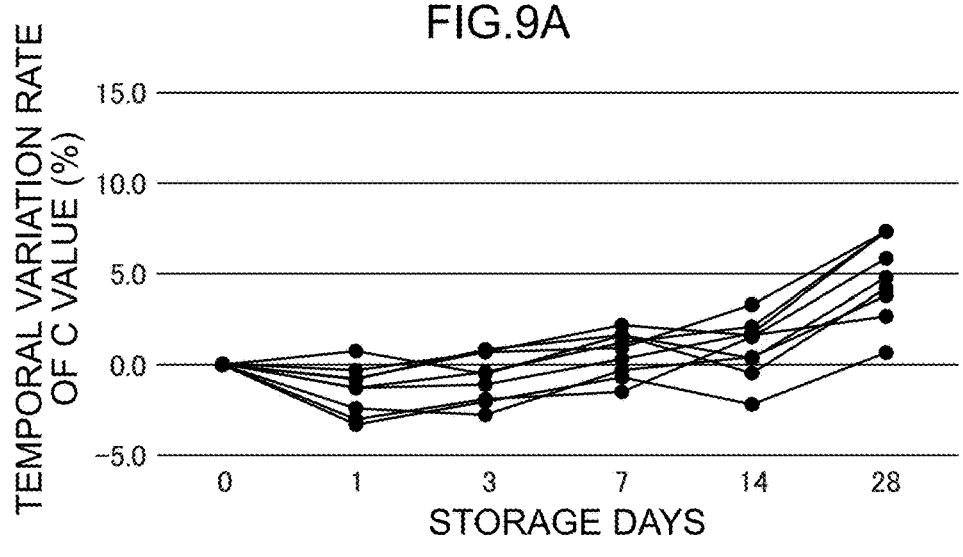
FIG. 9A is a graph illustrating a temporal change in a variation rate of the C value with respect to Day 0 for Specimen 1.
Figure 9B:
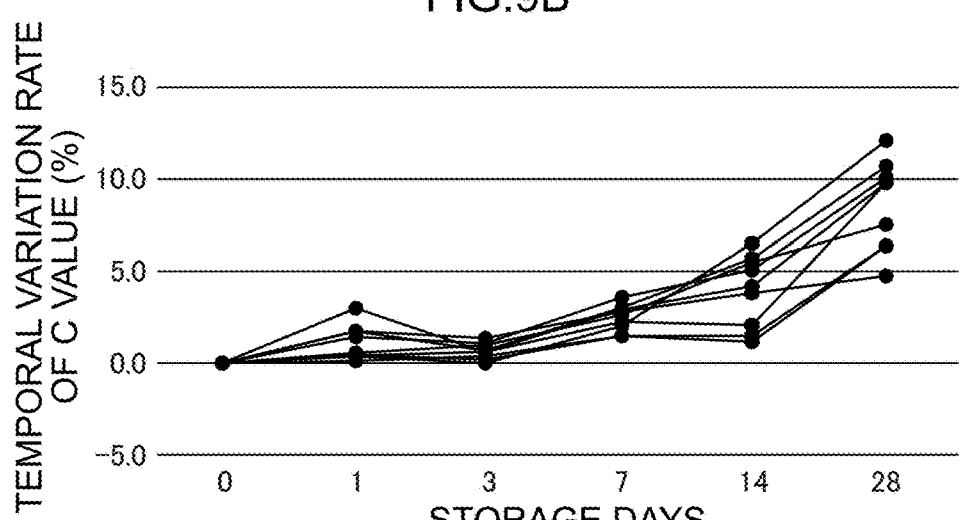
FIG. 9B is a graph illustrating a temporal change in a variation rate of the C value with respect to Day 0 for Specimen 2.
Figure 9C:
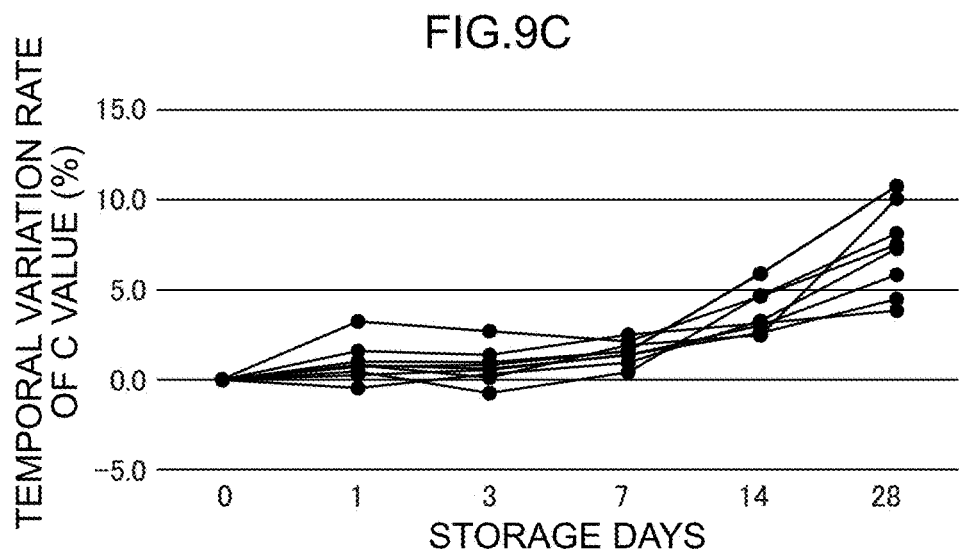
FIG. 9C is a graph illustrating a temporal change in a variation rate of the C value with respect to Day 0 for Specimen 3.

FIG. 8A to FIG. 8C are graphs obtained by plotting, for each blood collection tube, an average value of values obtained by double measurement at each measurement point for each of the same measurement data of each of Specimen 1 (FIG. 8A), Specimen 2 (FIG. 8B), and Specimen 3 (FIG. 8C) as in the first correction method, with the horizontal axis representing the number of days of storage and the vertical axis representing a value obtained by converting the measurement raw value of the C value into the international standardized value (unit: %). Furthermore, in FIG. 9A to FIG. 9C, a variation rate (temporal variation rate, unit: %) with respect to the C value on Day 0 is calculated from each C value in FIG. 8A to FIG. 8C, and plotted with the vertical axis and the storage days as the horizontal axis. Here, the temporal variation rate $(R_2)$ is a value calculated by the following Formula (6), where the C value on Day 0 is $C_0$ and the C value on Day n is $C_n$.

$$R_2 = (C_n - C_0)/C_0 \times 100 \tag{6}$$

In any of the specimens, regardless of the difference in the blood collection tube, the C value (FIG. 8A to FIG. 8C) increased as the number of storage days elapsed, and the temporal variation rate of the C value (FIG. 9A to FIG. 9C) also tended to increase accordingly.

Figure 10:
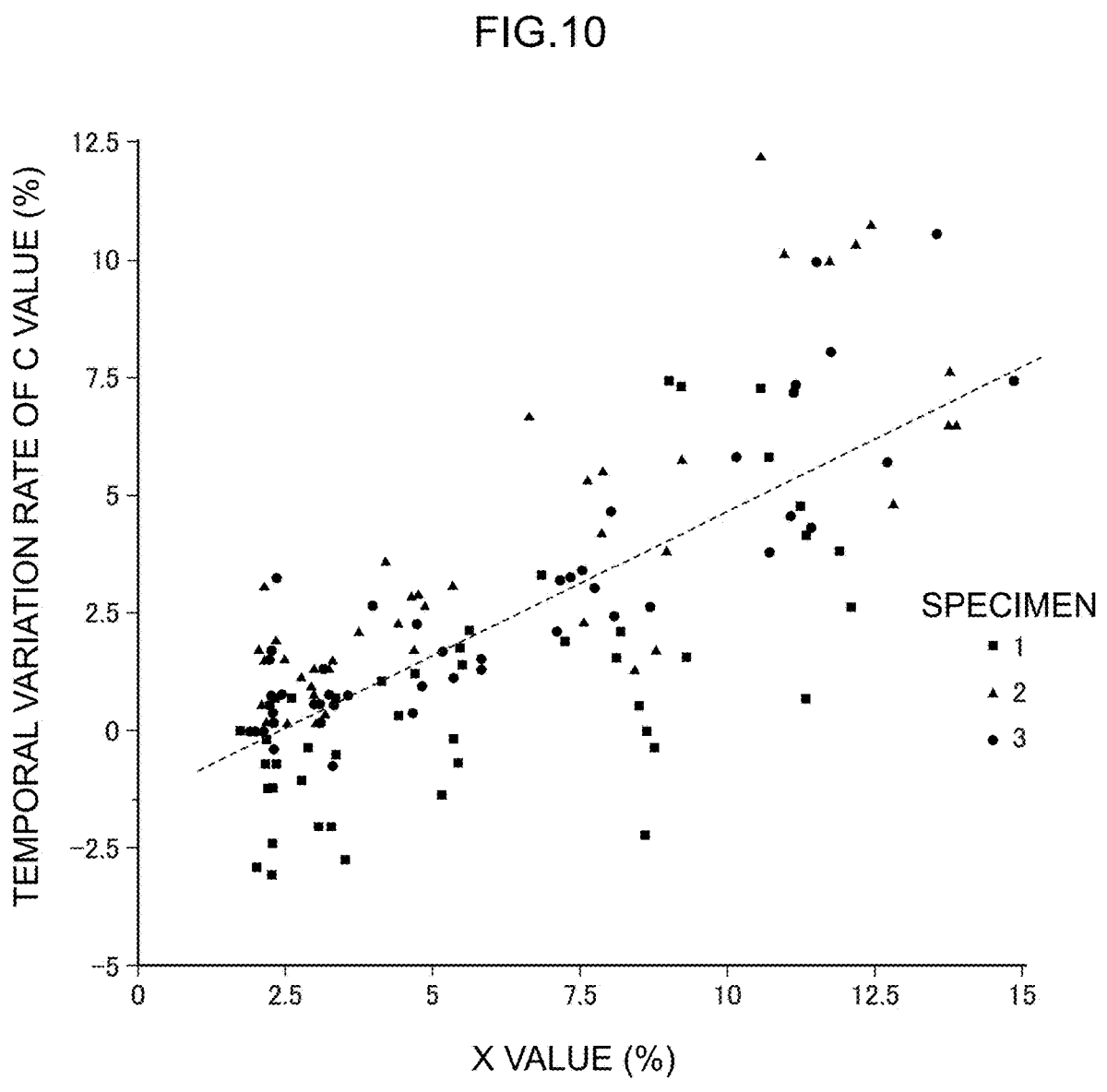

FIG. 10 is a scatter diagram illustrating a correlation between the temporal variation rate of the C value and the X value plotted on a graph for each measurement point. From this scatter diagram, it can be seen that there is a positive correlation between the X value and the variation rate of the C value. Furthermore, a broken line in the drawing indicates a regression line, and is expressed by the following Formula (7) when the temporal variation rate is y and the X value is x. Note that the correlation coefficient (r) of this regression line was 0.782.

$$y = 0.6323x - 1.4143 \tag{7}$$

Figure 11A:
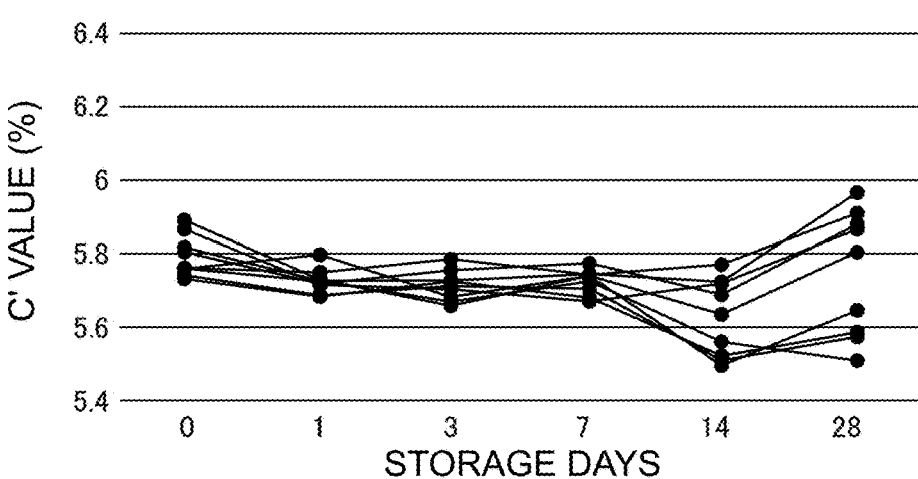
FIG. 11A is a graph illustrating a temporal change in the C' value for Specimen 1.
Figure 11B:
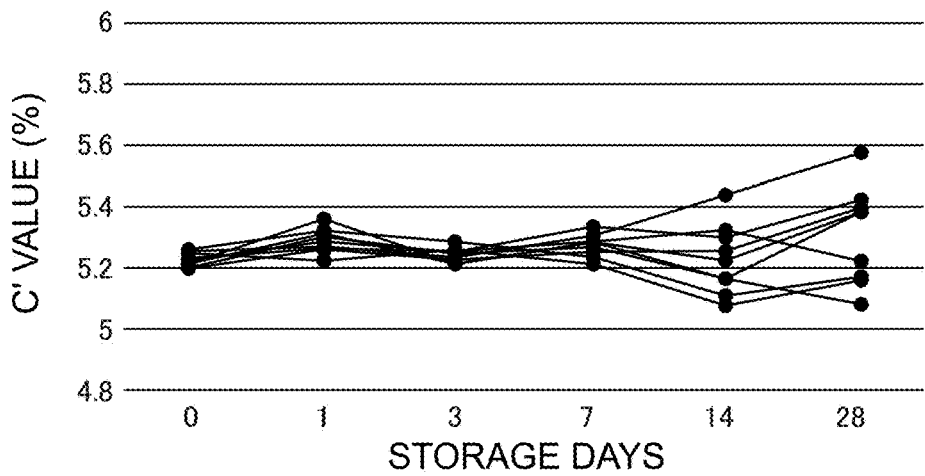
FIG. 11B is a graph illustrating a temporal change in the C' value for Specimen 2.
Figure 11C:
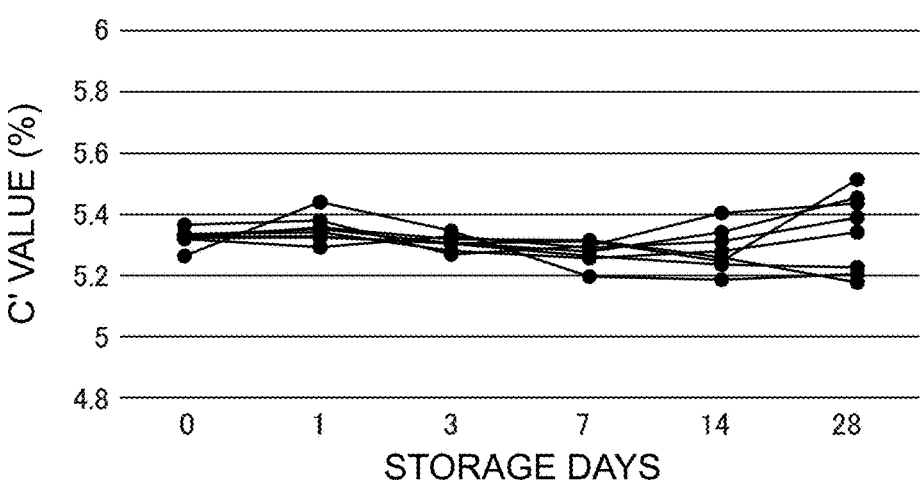
FIG. 11C is a graph illustrating a temporal change in the C' value for Specimen 3.
Figure 12A:
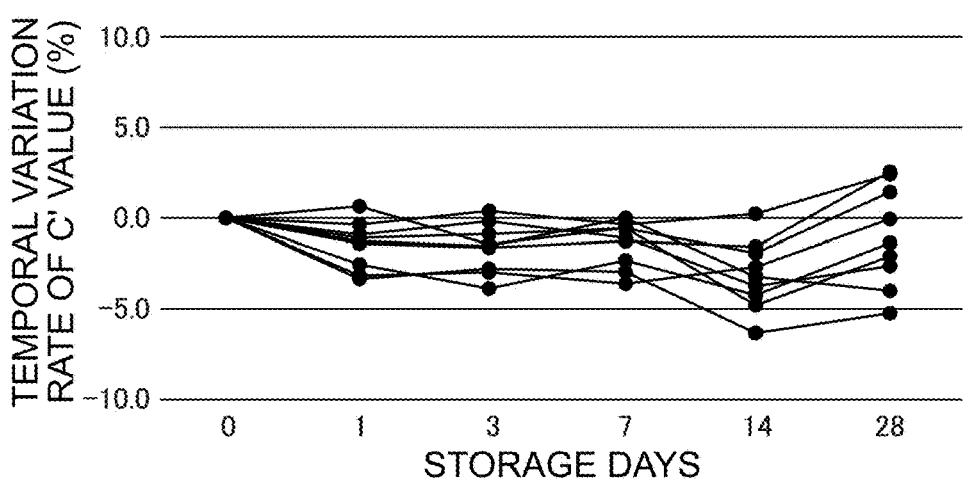
FIG. 12A is a graph illustrating a temporal change in a variation rate of the C' value with respect to Day 0 for Specimen 1.
Figure 12B:
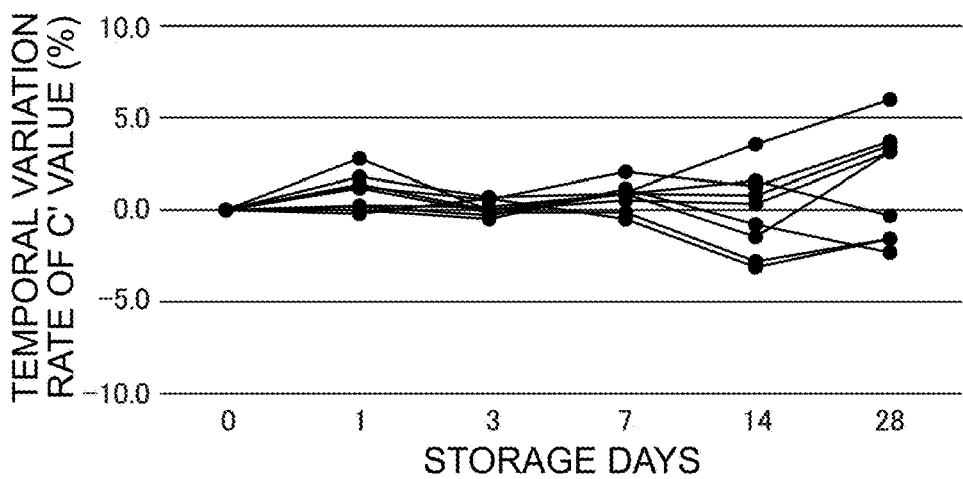
FIG. 12B is a graph illustrating a temporal change in a variation rate of the C' value with respect to Day 0 for Specimen 2.
Figure 12C:
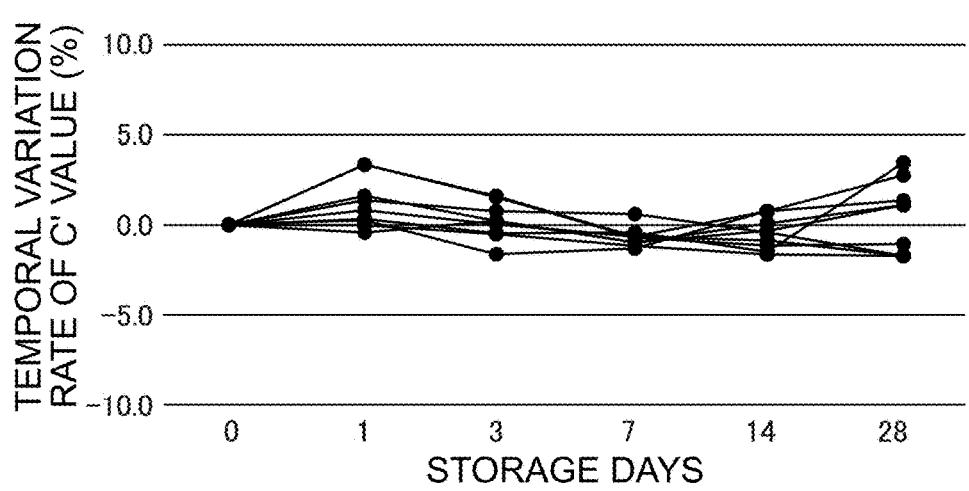
FIG. 12C is a graph illustrating a temporal change in a variation rate of the C' value with respect to Day 0 for Specimen 3.

Then, FIG. 11A to FIG. 11C illustrate plots in which the X value obtained from the blood specimen to be measured is taken as x, the value of y obtained by applying the x to the above Formula (7) is taken as the $R_1$ value, the value obtained by multiplying the $R_1$ value by the C value is subtracted from the C value to reduce the C value, and the corrected C' value is plotted on the horizontal axis with the number of storage days as in FIG. 8A to FIG. 8C. Furthermore, FIG. 12A to FIG. 12C are obtained by calculating the temporal variation rate with respect to the C' value on Day 0 from each C' value in FIG. 11A to FIG. 11C, respectively, and plotting this on the vertical axis and the number of storage days on the horizontal axis.

In any of the specimens, regardless of the difference in the blood collection tube, the increase in the C' value (FIG. 11A to FIG. 11C) was suppressed as compared with FIG. 8A to FIG. 8C even after the lapse of the number of storage days, and the temporal variation rate of the C' value (FIG. 12A to FIG. 12C) was leveled off.

The average, standard deviation, and coefficient of variation of the data before and after correction of each of Specimen 1 to Specimen 3 are shown in Table 3 below.

TABLE 3

| | Before Correction | | | After Correction | | |
| Specimen | Average | Standard Deviation | Coefficient of Variation | Average | Standard Deviation | Coefficient of Variation |
| --- | --- | --- | --- | --- | --- | --- |
| 1 | 5.83 | 0.14 | 2.4 | 5.72 | 0.10 | 1.8 |
| 2 | 5.37 | 0.17 | 3.1 | 5.26 | 0.09 | 1.6 |
| 3 | 5.42 | 0.15 | 2.7 | 5.30 | 0.07 | 1.3 |

From Table 3 above, it can be seen that since the coefficient of variation is smaller after correction than before correction, the accuracy of each measured value is improved.

INDUSTRIAL APPLICABILITY

The present disclosure can be used for measurement of stable HbA1c in a blood specimen using a hemoglobin separation analysis method based on cation exchange as a principle.

What is claimed is:

1. A method of measuring stable hemoglobin A1c comprising:

performing a hemoglobin separation analysis method based on cation exchange as a principle on a target blood specimen to obtain an analysis signal;

determining a C value, which is a peak value of a stable hemoglobin A1c peak, and an X value, which is a peak value of a specific peak appearing between the stable hemoglobin A1c peak and a hemoglobin A0 peak, from the analysis signal; and correcting the C value by applying the C value and the X value to a predetermined arithmetic expression to obtain a C' value that is a reduced value from the C value, wherein the arithmetic expression is determined based on a correlation between a C value and an X value obtained from a reference blood specimen having a known stable hemoglobin A1c value by the separation analysis method.

2. The method of measuring stable hemoglobin A1c according to claim 1, wherein:

the arithmetic expression includes an expression represented by $$Y=A \times X$$

and $$C'=C-Y,$$

wherein

A is a slope of a regression line between the X value and the C value, both of which are obtained from a plurality of reference blood specimens each having a known stable hemoglobin A1c value, X is the X value obtained from the target blood specimen, and C is the C value obtained from the target blood specimen.

3. The method of measuring stable hemoglobin A1c according to claim 2, wherein when a peak top detection time of the stable hemoglobin A1c peak is 0 and a peak top detection time of the hemoglobin A0 peak is 1, a peak appearing in a detection time of 0.1 or more and less than 0.65 is referred to as the specific peak.

4. The method of measuring stable hemoglobin A1c according to claim 2, wherein the correcting is executed in a case in which the X value exceeds a threshold value.

5. The method of measuring stable hemoglobin A1c according to claim 1, wherein:

the arithmetic expression includes an expression represented by $$R_1=a \times X+b$$

and $$C'=C-C \times R_1,$$

wherein a is a slope of a regression line between the X value and a temporal variation rate of the C value, both of which are obtained from a plurality of reference blood specimens each having a known stable hemoglobin A1c value, b is an intercept of the regression line, X is the X value obtained from the target blood specimen, and C is the C value obtained from the target blood specimen.

6. The method of measuring stable hemoglobin A1c according to claim 3, wherein, providing when a peak top detection time of the stable hemoglobin A1c peak is 0 and a peak top detection time of the hemoglobin A0 peak is 1, a peak appearing in a detection time of 0.1 or more and less than 0.65 is referred to as the specific peak.

7. The method of measuring stable hemoglobin A1c according to claim 5, wherein the correcting is executed in a case in which the X value exceeds a threshold value.

8. The method of measuring stable hemoglobin A1c according to claim 1, wherein when a peak top detection time of the stable hemoglobin A1c peak is 0 and a peak top detection time of the hemoglobin A0 peak is 1, a peak appearing in a detection time of 0.1 or more and less than 0.65 is referred to as the specific peak.

9. The method of measuring stable hemoglobin A1c according to claim 1, wherein the correcting is executed in a case in which the X value exceeds a threshold value.

10. A measurement device for stable hemoglobin A1c, comprising:

a memory that stores an arithmetic expression determined in advance based on a correlation between a C value, which is a peak value of a stable hemoglobin A1c peak, and an X value, which is a peak value of a specific peak appearing between the stable hemoglobin A1c peak and a hemoglobin A0 peak, by subjecting a reference blood specimen having a known stable hemoglobin A1c value to a hemoglobin separation analysis method based on cation exchange as a principle;

an analyzer that obtains an analysis signal by subjecting a target blood specimen to be measured to the hemoglobin separation analysis method based on cation exchange as a principle;

a first calculator that obtains a C value, which is a peak value of the stable hemoglobin A1c peak, and an X value, which is a peak value of a specific peak appearing between the stable hemoglobin A1c peak and the hemoglobin A0 peak, from the analysis signal; and a second calculator that calculates a C' value that is a reduced value from the C value, by applying the C value and the X value to the arithmetic expression.

11. The measurement device according to claim 10, wherein:

the arithmetic expression includes an expression represented by $$Y=A \times X$$

and $$C'=C-Y,$$

wherein

A is a slope of a regression line between the X value and the C value, both of which are obtained from a plurality of reference blood specimens each having a known stable hemoglobin A1c value, X is the X value obtained from the target blood specimen, and C is the C value obtained from the target blood specimen.

12. The measurement device according to claim 11, wherein when a peak top detection time of the stable hemoglobin A1c peak is 0 and a peak top detection time of the hemoglobin A0 peak is 1, a peak appearing in a detection time of 0.1 or more and less than 0.65 is referred to as the specific peak.

13. The measurement device according to claim 11, wherein the second calculator calculates a C' value in a case in which the X value exceeds a threshold value.

14. The measurement device according to claim 10, wherein:

the arithmetic expression includes an expression represented by $$R_1 = a \times X + b$$

and $$C' = C - C \times R_1,$$

wherein a is a slope of a regression line between the X value and a temporal variation rate of the C value, both of which are obtained from a plurality of reference blood specimens each having a known stable hemoglobin A1c value, b is an intercept of the regression line, X is the X value obtained from the target blood specimen, and C is the C value obtained from the target blood specimen.

15. The measurement device according to claim 14, wherein when a peak top detection time of the stable hemoglobin A1c peak is 0 and a peak top detection time of the hemoglobin A0 peak is 1, a peak appearing in a detection time of 0.1 or more and less than 0.65 is referred to as the specific peak.

16. The measurement device according to claim 14, wherein the second calculator calculates a C' value in a case in which the X value exceeds a threshold value.

17. The measurement device according to claim 10, wherein when a peak top detection time of the stable hemoglobin A1c peak is 0 and a peak top detection time of the hemoglobin A0 peak is 1, a peak appearing in a detection time of 0.1 or more and less than 0.65 is referred to as the specific peak.

18. The measurement device according to claim 10, wherein the second calculator calculates a C' value in a case in which the X value exceeds a threshold value.

\* \* \* \* \*